US006910377B1

(12) United States Patent
Richter et al.

(10) Patent No.: US 6,910,377 B1
(45) Date of Patent: Jun. 28, 2005

(54) FLUID RESERVOIR WITH LEVEL MEASUREMENT AND A DOSING SYSTEM, A WITHDRAWAL SYSTEM AND A COMBINED DOSING/WITHDRAWAL SYSTEM

(75) Inventors: Martin Richter, Munich (DE); Peter Woias, Munich (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 0 days.

(21) Appl. No.: 10/258,710

(22) PCT Filed: Apr. 28, 2000

(86) PCT No.: PCT/EP00/03878

§ 371 (c)(1),
(2), (4) Date: Feb. 26, 2003

(87) PCT Pub. No.: WO01/84091

PCT Pub. Date: Nov. 8, 2001

(51) Int. Cl.⁷ .............................................. G01F 23/00
(52) U.S. Cl. ................... 73/290 R; 73/304 C
(58) Field of Search .................. 73/304 C, 290 R

(56) References Cited

U.S. PATENT DOCUMENTS

| 5,224,375 A | 7/1993 | You et al. .................. 73/54.08 |
| 5,463,228 A | 10/1995 | Krause ....................... 250/577 |
| 5,588,963 A * | 12/1996 | Roelofs ....................... 604/65 |
| 5,790,422 A * | 8/1998 | Power et al. .............. 73/304 R |

FOREIGN PATENT DOCUMENTS

| DE | 43 06 064 | 2/1993 | ........... G01F 23/26 |
| DE | 19736178 C * | 1/1999 | ........... G01N 27/22 |
| DE | 19944331 c * | 8/1999 | ........... G01F 23/24 |
| EP | 458 405 | 11/1991 | ............. B01L 3/00 |
| JP | 62201068 | 2/1989 | ........ G01N 33/497 |

* cited by examiner

Primary Examiner—Hezron Williams
Assistant Examiner—Tamiko Bellamy
(74) Attorney, Agent, or Firm—Michael A. Glenn; Glenn Patent Group

(57) ABSTRACT

A liquid reservoir with level measurement includes a base body (10) and a channel (12) implemented in the base body and comprising an inlet (14) and an outlet (16), the dimensions of the cross-section of the channel being selected such that a liquid (18) which may be filled into the channel forms a liquid meniscus (20) which demarcates a section (12b) of the channel which is filled with liquid from an unfilled section (12a) of the channel in which no liquid is present, the position of the meniscus in relation to the channel being substantially independent of the orientation of the liquid reservoir. The liquid reservoir further includes detection means (32, 22, 24) for detecting the position of the liquid meniscus and/or the channel so as to obtain, from the position of the liquid meniscus, the level and/or a change in the level of the liquid reservoir. The inventive liquid reservoir is suitable as a low-priced drug reservoir particularly in connection with a capacitive level detection.

17 Claims, 5 Drawing Sheets

FLUID RESERVOIR WITH LEVEL MEASUREMENT AND A DOSING SYSTEM, A WITHDRAWAL SYSTEM AND A COMBINED DOSING/WITHDRAWAL SYSTEM

FIELD OF THE INVENTION

The present invention relates to a liquid reservoir and in particular to a liquid reservoir with level measurement which may be used in connection with a dosing system, a withdrawal system or a dosing system/withdrawal system.

BACKGROUND OF THE INVENTION AND PRIOR ART

In the field of medicine but also in other fields of technology there is a need for determining amounts of liquid so as to carry out an absolute liquid measurement or to dose certain amounts of liquid. For determining the amount of liquid dispensed, it is no longer the amount of liquid per se that is decisive but the change in the amount of liquid over time.

Particularly in the field of medicine there is also a strong need for liquid reservoirs for drugs. Here it is often required to administer accurately dosed amounts of liquid. In addition, there is a requirement that the liquid reservoirs are designed in a low-cost manner since they are often disposable articles which cannot be reused for hygienic reasons.

In the U.S. Pat. No. 5,463,228, an apparatus for an automatic exact dosing of small amounts of liquid in a medical analysis system is disclosed, the apparatus comprising a transparent measuring tube with a capillary tube having an internal diameter of less than 1 mm, the measuring tube further comprising a liquid transfer opening at one end of same, the liquid transfer opening being provided for drawing in a liquid. The apparatus further includes liquid phase boundary detection means for automatic detection of a liquid phase boundary in the measuring tube, an electrical position signal of a position of the liquid phase boundary being generated. The detection of the liquid phase boundary takes place in an optical manner, to be precise using a light source and a CCD line array.

In DE 4306061 A1, an apparatus for detecting the level of a capillary overflow channel is disclosed. The apparatus includes a channel connected, at one end, to an inflow which is connected to a reservoir via a controllable valve. At the other end of the channel there is a further channel of a larger diameter which is connected to an outflow. An overflow channel which is designed in a helical manner around the channel and which extends between a first detection electrode and a second detection electrode is in fluidic communication with the channel so as to capacitively detect the level of the overflow channel. The overflow channel acts as a buffer volume. If a level is detected in the overflow channel, the valve between the reservoir and the inflow is closed until it is detected that the overflow channel is empty. Then the valve is opened again until the overflow channel again has a level, whereupon the valve is closed again. The control device may be employed for separating an ink reservoir in plotter pens, recording devices, medical apparatus or apparatus used in process engineering.

SUMMARY OF THE INVENTION

It is an object of the present invention to provide a dosing system or a combined dosing/withdrawal system with a liquid reservoir.

In accordance with a first aspect of the invention, this object is achieved by a dosing system, comprising: a liquid reservoir with level measurement, the liquid reservoir comprising: a base body; a channel implemented in the base body and having an inlet and an outlet, the dimensions of a cross-section of the channel being selected such that a liquid which may be filled into the channel forms a liquid meniscus which demarcates a section of the channel filled with liquid from an unfilled section of the channel in which no liquid is present, the position of the liquid meniscus in relation to the channel being substantially independent of the orientation of the liquid reservoir; and detection means for detecting the position of the liquid meniscus in relation to the channel so as to obtain the level and/or a change in the level of the liquid reservoir from the position of the liquid meniscus; means for exhausting a liquid which may be filled into the liquid reservoir, the means for exhausting being connected to the outlet, and/or means for pumping gas into the unfilled section of the channel, the means for pumping being connected to the inlet; and control means for controlling the means for exhausting and/or the means for pumping, the control means being coupled to the detection means of the liquid reservoir so as to dispense a predetermined amount of liquid from the channel via the outlet of the channel, depending on the position of the liquid meniscus; wherein the detection means are capacitive and comprise two electrodes electrically insulated from each other and mounted on the base body such that both the filled and the unfilled section of the channel extend between same, whereby an electric field that may be generated between the two electrodes is present both in the filled section of the channel and in the unfilled section of the channel, and whereby a change in the position of the liquid meniscus leads to a proportional change in capacitance.

In accordance with a second aspect of the invention, this object is achieved by a combined dosing/withdrawal system, comprising: a liquid reservoir with level measurement, the liquid reservoir comprising: a base body; a channel implemented in the base body and having an inlet and an outlet, the dimensions of the channel cross-section being selected such that a liquid which may be filled into the channel forms a liquid meniscus which demarcates a section of the channel filled with liquid from an unfilled section of the channel in which no liquid is present, the position of the liquid meniscus in relation to the channel being substantially independent of the orientation of the liquid reservoir; and detection means for detecting the position of the liquid meniscus in relation to the channel so as to obtain the level and/or a change in the level of the liquid reservoir from the position of the liquid meniscus; first means for pumping a liquid into the liquid reservoir and/or for exhausting a liquid from the liquid reservoir, the first means for pumping and/or exhausting being connected to the outlet, and/or second means for exhausting gas from the unfilled section of the channel and/or for pumping gas into the unfilled section of the channel, the second means for exhausting and/or pumping being connected to the inlet; and control means for controlling the first means and/or the second means, the control means being coupled to the detection means of the liquid reservoir so as to convey a predetermined amount of liquid into the channel via the outlet of the channel and/or dispense a predetermined amount of liquid from the channel via the outlet of the channel, depending on the position of the liquid meniscus, wherein the detection means are capacitive and comprise two electrodes electrically insulated from each other and mounted on the base body such that both the filled and the unfilled section of the channel extend between same, whereby an electric field that may be generated between the two electrodes is present both in the filled section of the channel and in the unfilled section of the channel, and whereby a change in the position of the liquid meniscus leads to a proportional change in capacitance.

The present invention is based on the findings that accurate level measurement of a liquid in a liquid reservoir may be achieved if the liquid reservoir comprises a channel implemented in a base body and having an inlet and an outlet, the dimensions of the cross-section of the channel being selected such that a liquid which may be filled into the channel forms a liquid meniscus which demarcates a section of the channel filled with liquid from an unfilled section of the channel, i.e. a section of the channel in which no liquid is present, the position of the meniscus in relation to the channel being substantially independent of the orientation of the liquid reservoir. For level measurement, detection means for detecting the position of the liquid meniscus in relation to the channel are used so as to obtain the level and/or a change in the level of the liquid reservoir from the position of the liquid meniscus.

Generally speaking, the position and shape of the liquid meniscus are dependent on the gravity on the one hand as well as on the surface tension between the liquid and air, and on the interfacial tension between the drug and the reservoir material on the other hand. The last two parameters define the wetting angle. In accordance with the invention, the dimensions of the cross-section of the channel are selected to be so small that the shape of the liquid meniscus is determined, above all, by the surface and interfacial tensions and no longer by the gravity or other forces, i.e. rotational force, vibrational force, magnetic forces etc. Depending on the liquid properties and the channel material, the surface tension (and also the interfacial tension) will be dominant relative to gravity in channels which are circular in cross-section and have diameters smaller than 0.5 to 3 mm. Here gravity no longer is important, i.e. the liquid meniscus will not significantly change its position even if the liquid reservoir is in any position desired, be it that same is tilted, upside down or arranged in any other way.

Depending on the implementation, a capacitive detection of the position of the level meniscus in relation to the channel, or even optical detection as well as other detection means may be employed. All detection means are based on different properties of the unfilled section of the channel as compared with the filled section of the channel.

The present invention is particularly advantageous in that it may be implemented in a very low-cost manner, in particular if capacitive detection methods are used, since in this case only two electrodes must be mounted in relation to the channel, by which electrodes an electric field may be generated which extends both in the unfilled section and in the filled section of the channel. This advantage of low cost is relevant in particular on the intensely competitive mass market of disposable products in the field of medicine.

The dosing system or the combined dosing/withdrawal system of the present invention includes a liquid reservoir whose level may be determined more accurately in a manner which is completely independent of the position and location of the liquid reservoir. This, in turn, is highly important in liquid reservoirs for accommodating drugs, since such liquid reservoirs are carried by patients, and hence constantly change their position and orientation, in particular if such liquid reservoirs are used for constant dosing of drugs. Due to the inventive dimensioning of the channel, however, the liquid meniscus always stays in the same position, since its position no longer depends on gravity but merely on the surface tension of the drug and on the interfacial tension between the drug and the channel wall.

A further advantage of the present invention is that the container volume of the liquid reservoir may still take on considerable dimensions with the inventive channel. This can be achieved, on the one hand, by the fact that the channel is arranged in the base body in the shape of a meander, so that a maximum channel length results in comparison with the external dimensions of the base body. If space requirements for the container are not decisive, it is alternatively also possible, in principle, to make the volume very large since the formation of a meniscus whose position in the channel is substantially independent of gravity does not depend on the cross-sectional area of the channel but on the shape of the cross-section of the channel, more specifically on the smallest dimension of the channel cross-section. If a rectangular channel is considered, a meniscus will form whenever a side length of the channel cross-section is dimensioned to be so small that the surface tension of the liquid leads to the formation of a meniscus. The other side length of the channel cross-section, however, may basically take on indefinitely high values, so that the container volume of the liquid reservoir may be adjusted within broad limits. For practical applications, in particular in the field of drug dosing system, volumes in the range of 0.1 to 50 ml are sufficient, however, so that the inventive liquid reservoirs are still convenient.

A further advantage of the present invention is that, if the base body is implemented as a hose, a commercially available hose with a correspondingly small cross-sectional diameter may easily be used as a liquid reservoir, since it must be supplemented merely by capacitive detection means, for example, so as to achieve a low-cost, flexible and accurate liquid reservoir.

It shall be pointed out that the dimensions of the channel cross-section do not necessarily have to be consistent across the length of the channel. Any increases or decreases in the cross-section may readily be calibrated out and/or taken into account via a conversion factor, which is dependent on the meniscus position, in determining the level volume.

A further advantage of the present invention is that, due to the relatively small channel dimensions, the meniscus concept and a capacitive measurement principle complement each other in a nearly optimum manner. Generally speaking, the smaller the distance between the capacitance electrodes, the higher a capacitance measured. Thus the meniscus also is the more stable, the smaller the dimensions of the channel are. With regard to the capacitive measurement principle, however, this means that depending on the geometry and the dielectric parameters of the liquid and the reservoir material, a sufficiently high sensitivity occurs in the form of a sufficiently large change in capacitance in the movement of the meniscus, which is determined by a discharge of the liquid from the liquid reservoir.

A further advantage of the present invention is that by means of low-cost but efficient concepts, the evaporation of the liquid in the liquid reservoir may be reduced or fully eliminated, depending on the requirements, without necessitating expensive measures.

BRIEF DESCRIPTION OF THE DRAWINGS

Preferred embodiments of the present invention will be explained in detail below with reference to the accompanying figures, in which.

DETAILED DESCRIPTION OF PREFERRED EMBODIMENTS

Figure 1:
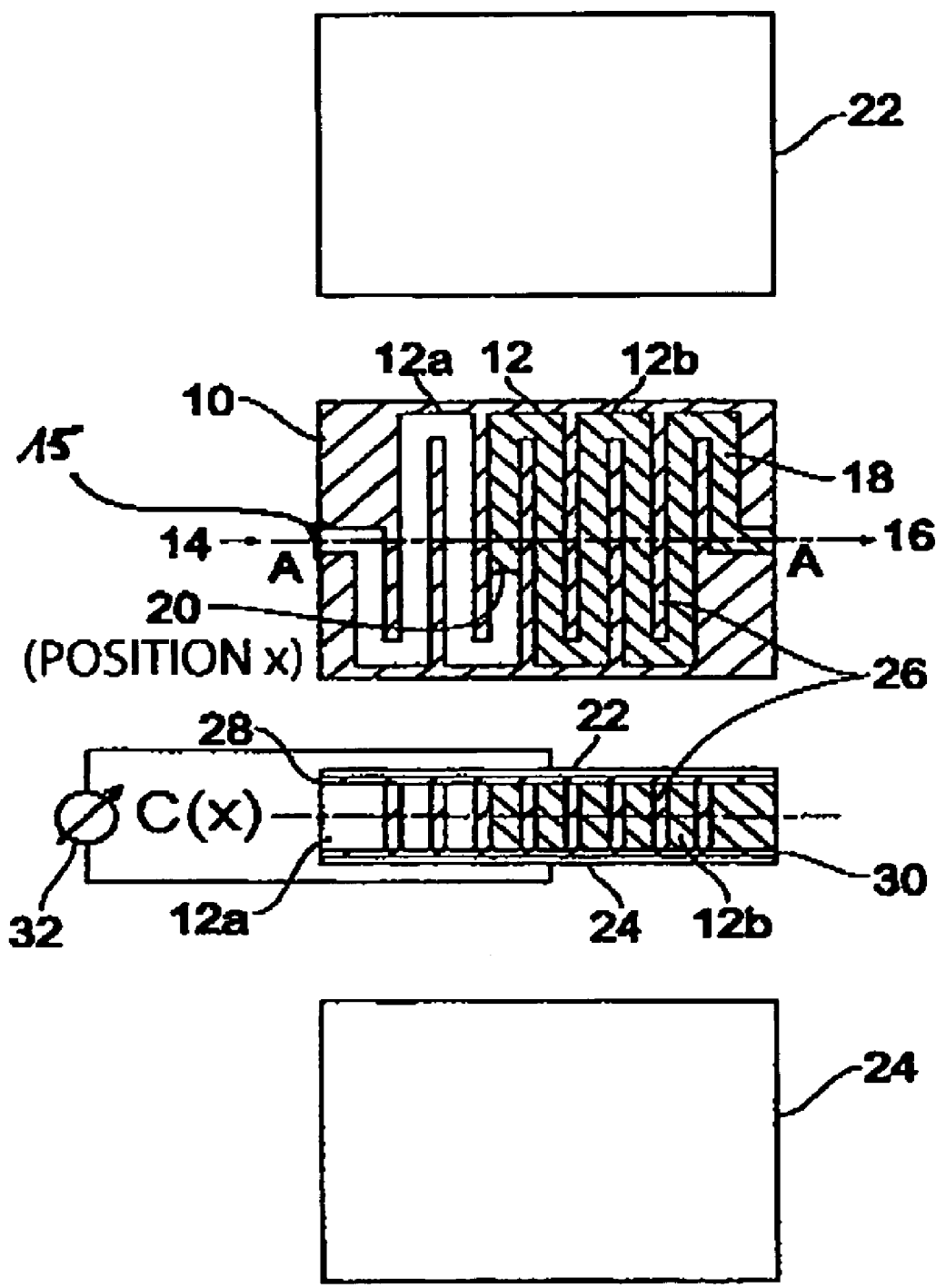
FIG. 1 shows a detailed representation of an inventive liquid reservoir with level measurement using capacitive detection.

FIG. 1 shows an inventive liquid reservoir with level measurement, wherein the preferred capacitive detection principle is employed. The inventive liquid reservoir includes a base body 10, wherein a preferably meander-shaped channel 12 is formed which comprises an inlet 14 and an outlet 16. The dimensions of the channel cross-section are selected such that a liquid 18 which may be filled into the channel forms a liquid meniscus 20 dividing the channel into a unfilled section 12a and in a filled section 12b, shown in a hatched manner in FIG. 1. The unfilled section 12a of the channel extends from the inlet 14 to the liquid meniscus-20, whereas the filled section 12b of the channel extends from the liquid meniscus 20 to outlet 16. In the unfilled section 12a of the channel there is preferably air. This section preferably has ambient pressure. Apart from any undesired gas bubbles that may be present, the filled section 12b is filled entirely with the liquid 18.

If the inventive liquid reservoir is employed as a drug reservoir in accordance with its preferred application, the liquid 18 is any drug in the liquid phase. Alternatively, the inventive liquid reservoir may also be used for accommodating other liquids.

In a preferred implementation of the present invention, as is shown in FIG. 1, a capacitive detection principle is employed. For this purpose, two electrodes 22 and 24 are deposited on the base body such that an electric field, which may be generated between the two electrically insulated electrodes, extends both in the filled section 12b and in the unfilled section 12a, so that a change in the position of the liquid meniscus 20 leads to a proportional change in capacitance due to the different relative permittivities of the drug 18 and of the air in the unfilled section 12a. Depending on the implementation of the electrodes, of the channel cross-section and of the design of the channel, a linear connection may be achieved between the change in capacitance and the change in the path of the liquid meniscus 20.

The second but lowest partial image of FIG. 1 shows a cross-section through the inventive liquid reservoir along the line AA of the second but highest partial image of FIG. 1. The inventive liquid reservoir includes the one electrode 22, which is also referred to as cap electrode due to the representation shown in FIG. 1, as well as the other electrode 24, which is also referred to as bottom electrode. In addition, the channel is represented by its unfilled section 12a and by its filled section 12b, which is drawn in a hatched manner. The meandering nature of the channel 12 is expressed by ridges 26 of the base body, which separate the individual channel sections from each other. As is shown in FIG. 1, the electrodes 22, 24 are insulated from the channel by insulating layers 28, 30, respectively. This is necessary if the liquid 18 is electrically conductive. If, however, the liquid 18 is electrically insulating anyway, the insulating layers 28, 30 may be dispensed with, and the bottom electrode 24 and the cap electrode 22 may directly demarcate the channel 12 toward the top and toward the bottom. However, in the case of a drug reservoir, medical aspects are also to be taken into account here with regard to material provisions, material selection or drug substance, i.e. whether same may be contacted directly with electrodes to which a voltage is applied.

Finally, the inventive liquid reservoir includes detection means 32 which are capacitance measuring means in the preferred embodiment of the present invention shown in FIG. 1. Depending on the position x of the liquid meniscus 20 in relation to the channel 12, a capacitance C(x) is measured by the detection means 32.

It shall be pointed out at this point that instead of the capacitive detection means, optical detection means, for example, may also be used which are arranged to scan the channel in a detection passageway, the liquid meniscus being established if either light transmitted through the channel or light reflected by the channel floor changes from a high level to a low level. In the event of detection means operating in an optical manner it is necessary, however, that at least the cap or the bottom of the channel 12 be at least partially transparent to the wavelength of the light used. A suitable material for the base body is, for example, the optically transparent material of polycarbonate, which advantageously may be processed by injection molding.

Other detection techniques, such as inductive methods, may also be used as long as the quantity to be measured is influenced by properties of the filled section 12b of the channel compared with properties of the unfilled section 12a of the channel.

Figure 2:
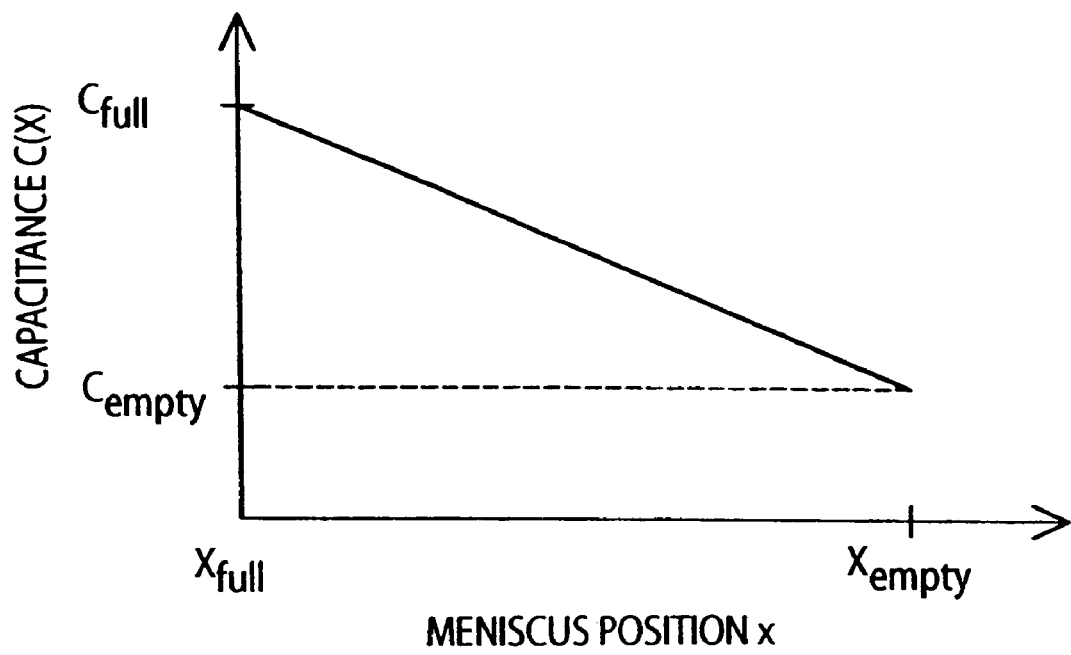
FIG. 2 shows a graphic representation of the course of capacitance versus the meniscus position for the inventive liquid reservoir of FIG. 1.

FIG. 2 shows a basic course of capacitance of the capacitance C(x) versus the meniscus position x. The marking $x_{full}$ indicates the case wherein the maximum filling quantity as has been directed has been filled into the inventive liquid reservoir. As will be further explained, this is not necessarily the maximum filling quantity. Instead, it is preferred that an unfilled section 12a of the channel still remain so as to minimize the evaporation of the liquid. This means that the liquid meniscus 20 does not necessarily extend to the outlet 14 even with the channel fully filled. The marking $x_{empty}$ shows the position of the liquid meniscus when the inventive liquid reservoir is emptied as directed. However, the liquid meniscus 20 must not necessarily be located directly at the outlet 16, if any residual liquid is to remain in the liquid reservoir. In the case of a dielectric constant of the liquid 18 in the filled section 12b, which is higher than the dielectric constant of the medium in the unfilled section 12a, which usually will be air, the capacitance of the inventive liquid reservoir is the highest when the liquid reservoir has its maximum level, as directed. This capacitance value is referred to as $C_{full}$ in FIG. 2. In the opposite case wherein the inventive liquid reservoir is emptied to a maximum, the capacitance, which is still present then, is referred to as $C_{empty}$. So as to achieve a high sensibility for the purposes of achieving as good a measuring accuracy as possible, the aim is to maximize $C_{full}$ whereas $C_{empty}$ is minimized. In addition, the meandering length is maximized, depending on the form of application, for achieving as large a filling volume as possible. To this end it is necessary that the insulating layers 28, 30 (FIG. 1) be selected to be as thin as possible, whereas the meandering area becomes as large as possible.

From this it can be seen that the demand, which exists on the one hand, for a stable liquid meniscus which is independent of the location, and the demand, which exists on the other hand, for as large a meandering area as possible for achieving a high capacitive sensitivity complement each other in an optimum manner. Therefore detection means which operate in a capacitive manner are preferred for the inventive liquid reservoir.

The basic concept described in FIG. 1 is disadvantageous with regard to the fact that both the bottom electrode 22 and the cap electrode 24 are not optically transparent. Any gas bubbles that may be present in the filled section 12b of the channel are not detectable.

To remedy this property, either the cap electrode or the bottom electrode or both electrodes may be implemented as grid electrodes, so that the filling quality of the reservoir may be evaluated either manually or automatically.

Figure 3:
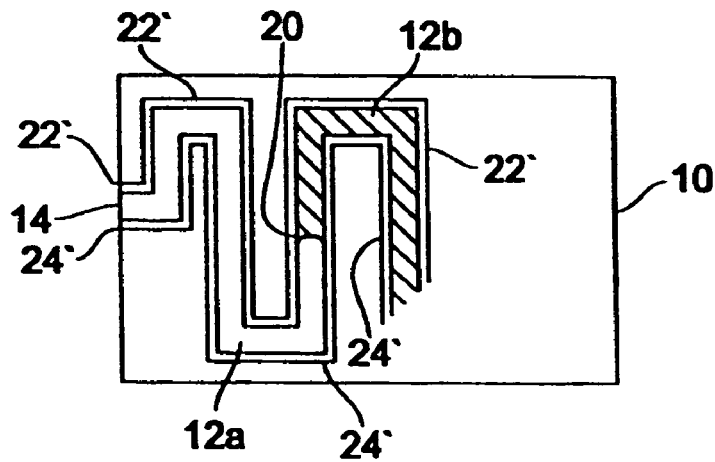
FIG. 3 a top view of a base body of an inventive liquid reservoir which also uses capacitive detection of the position of the meniscus, wherein, however, vertical electrodes are present.

As is shown in FIG. 3, an arrangement of vertical electrodes 22', 24' may be used instead of the electrodes which extend substantially in parallel with the channel, such that the electrodes are not applied to the base body 10 as in the embodiment shown in FIG. 1, but are applied vertically to the main surfaces of the base body. The electrodes 22', 24' follow, as it were, the channel 12 on both sides of same. If the cap of the channel or the bottom of the channel or both, that is cap and bottom, are implemented in an optically transparent manner, it is readily possible, in this case, to recognize and/or to locate any gas bubbles existing in the filled section 12b of the channel.

Figure 4:
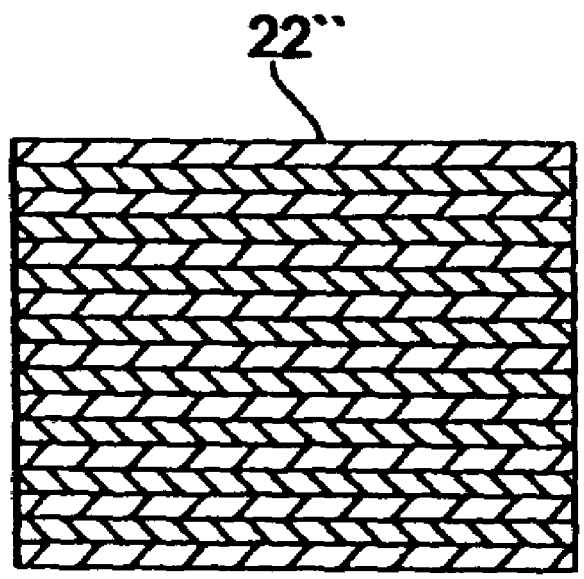
FIG. 4 shows a top view of the bottom electrode and the cap electrode, which are each comprised of a plurality of individual electrodes in the embodiment shown in FIG. 4.
Figure 4:
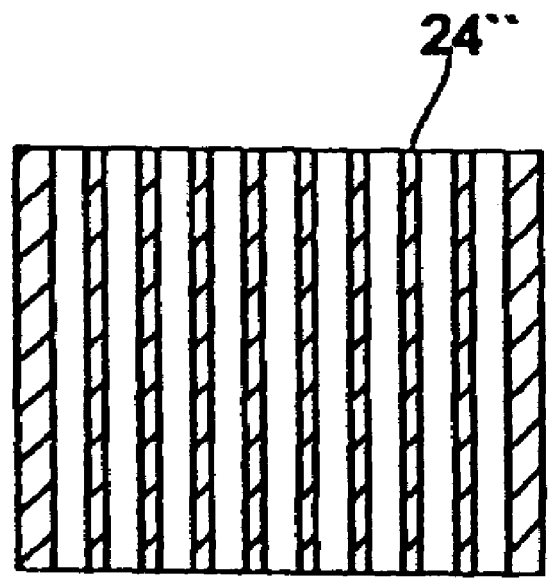

FIG. 4 shows a further variant of the cap electrode 22'' as well as of the bottom electrode 24''. Here both electrodes 22'' and 24'' are no longer implemented as a continuous area but as individual electrode strips separated from each other such that an individual capacitance forms between an electrode strip of the bottom electrode and an electrode strip of the cap electrode. By interrogating several electrodes on the top and bottom sides in pairs, gas bubbles within the filled section 12b of the channel may also be recognized and/or located.

Figure 5:
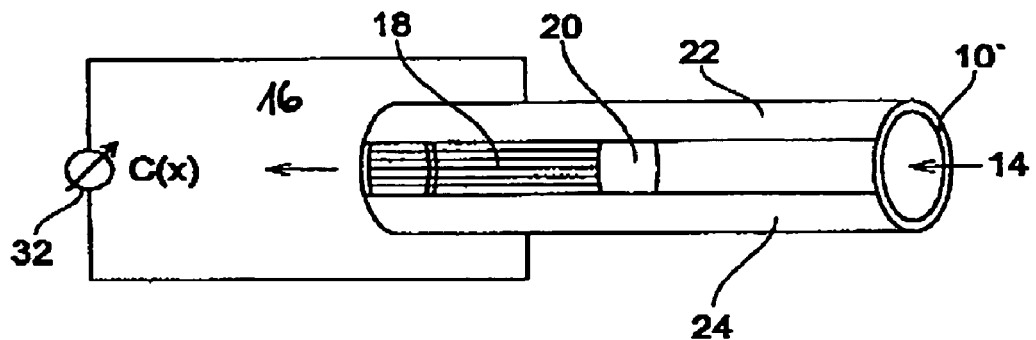
FIG. 5 shows a perspective view of an inventive liquid reservoir with level measurement, wherein the base body is implemented as a hose.

FIG. 5 shows an alternative implementation of the inventive liquid sensor, wherein the base body 10' is implemented as a hose. On the top side and on the bottom side of the hose, electrodes 22 and 24, respectively, are applied, which are contacted and provided with capacitive detection means just like in the embodiment shown in FIG. 1, so as to determine the position of the meniscus 20 along the length of the hose 10'. It shall be pointed out that in the embodiment shown in FIG. 5 no additional existing insulating layers are required since the wall of the hose itself acts as an insulating layer so as to carry out conductive decoupling of the liquid 18 and the two electrodes 22, 24.

Figure 6:
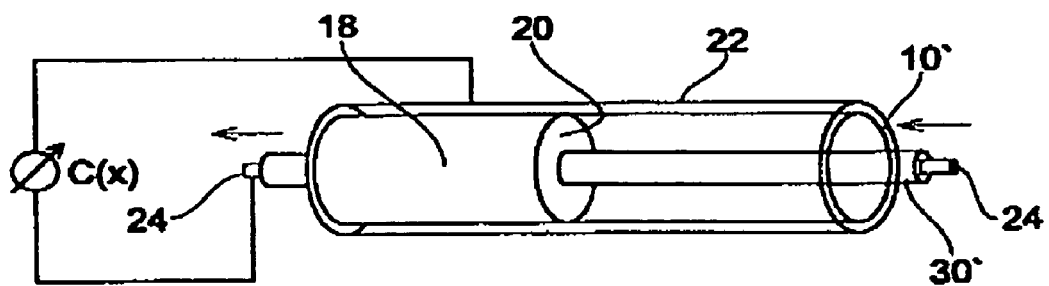
FIG. 6 shows a perspective view of an inventive liquid reservoir with level measurement, wherein the base body is also implemented as a hose, as in FIG. 5, wherein, however, a coaxial arrangement of the two electrodes is used.

FIG. 6 shows a further implementation of the inventive liquid reservoir, wherein the base body is also implemented as a hose 10'. As opposed to the embodiment shown in FIG. 5, a coaxial, as it were, electrode arrangement is used in the embodiment shown in FIG. 6. The outer surface of the hose 10' here is fully surrounded by the one electrode 22, whereas the other electrode 24 is formed by a conductor 24 located in the hose, which conductor 24 is conductively decoupled from the liquid 18 by an insulating layer 30'. The electrode 24 may either be loose in the hose or may be fixed in the center in a concentric manner. If same is loose in the hose, it is necessary, however, that the drug reservoir in the form of a hose be kept still during dosing system. If its position is changed, same must be recalibrated so as to take into account any changes between the insulated inner electrode 24 in relation to the outer electrode 22 arranged on the sheathing of the hose.

In the following, dimensioning criteria of the inventive liquid reservoir, shown in FIG. 1, having a channel which is folded in a meander-like fashion shall be addressed. As has already been explained with reference to FIG. 2, the aim is to minimize the empty capacitance $C_{empty}$ and to maximize the full capacitance $C_{full}$. The empty capacitance results from connecting in parallel a channel capacitance of the channel filled with air and a so-called base body capacitance formed by the frame of the base body and the ridges 26 (FIG. 1) of the base body. It follows from an examination that for as small an empty capacitance as possible a material should be used for the base body which has a low dielectric constant. Further it is preferred to keep the surface areas of the ridges and of the frame as small as possible and/or to apply the electrode only to the channel, if possible, but not too much above an area of the base body which is not occupied by the channel.

The useful capacitance results from the difference between $C_{full}$ and $C_{empty}$. It should be as large as possible. This it achieved by making the meandering surface as large as possible in comparison with the area occupied by the ridges and the frame. In addition, both the channel cap and the channel bottom should be kept as thin as possible, as has already been discussed.

In summary, it shall be established that the inventive liquid reservoir with level measurement is designed such that in the event that the reservoir is emptied, the liquid meniscus which represents the interface between the liquid and air, is guided in a defined manner so that the level of the reservoir is measured by suitable detection methods. The vascular walls of the reservoir are preferably designed such that the diameter of the reservoir is small compared to the length of the reservoir. This may be achieved, on the one hand, by a channel which is folded in a meander-like fashion or, on the other hand, by a long hose.

A disturbance variable for the level measurement and/or for the operation of liquid reservoirs altogether is the evaporation of the liquid. It is particularly at the meniscus that the liquid can evaporate. During evaporation, molecules of liquid pass into the gas phase. This effectively leads to a small undesired movement of the meniscus, even though nothing is being dosed. The evaporation rate, i.e. the amount of drugs passing into the gas phase per time unit, above all depends, in addition to the saturation of air with drug molecules, also on the amount of free surface area between drug and air. The smaller the diameter of the channel, the smaller the disturbing evaporation.

The evaporation may have a disruptive effect particularly in the long term, for example if the reservoir filled is stored over a relatively long period of time. To further reduce evaporation, suitable measure may be taken.

One measure is not to fully fill the liquid reservoir, so that a suitably long stretch of air remains. Along this unfilled section of the channel, a concentration gradient of molecules of liquid that have passed into the gas phase will form. The longer this diffusion path for molecules of liquid that have passed into the gas phase, the smaller the resulting evaporation will be.

Another measure is to significantly reduce the stretch of air at one location, for example to 0.05 mm. Thereby the exchange of molecules between the liquid in the filled section of the channel and the gas in the unfilled section of the channel is further reduced.

A further measure is to seal the air-side inlet opening with a semi-permeable membrane 15 which is only permeable for air molecules but not for drug molecules, such that a rapid saturation of the enclosed air with the drug is achieved. This sealing may entail the further advantage of a germ-free seal, particularly for liquid reservoirs with drugs.

In summary it can therefor be established that the smaller the dimensioning of the channel cross-section is chosen to be, the more significant the inventive advantages become. The exact measures, however, will depend on the liquid which is immediately used and on the material from which the interior wall of the channel is formed.

A field of application of the liquid reservoir consists in the inventive dosing system comprising, in addition to an inventive liquid reservoir, means for exhausting liquid which may be filled into the liquid reservoir, which means are connected to the outlet, and/or means for pumping gas into the unfilled section, which means are connected to the outlet. The inventive dosing system further includes control means for controlling the means for exhausting and/or the means for pumping, the controlling means being coupled to the detection means of the liquid reservoir so as to dispense, depending on the position of the liquid meniscus, a predetermined amount of liquid from the channel via the outlet of the channel.

The dosing system may further be converted into a withdrawal system. In this case the means connected to the "outlet" are implemented as a pump so that the liquid to be withdrawn from the body, for example, is conveyed into the liquid reservoir via the outlet. Alternatively, this can be achieved in that the means connected to the inlet are implemented as suction means.

The dosing system and the withdrawal system may, in accordance with the invention, further be combined such that in the event of only one existing pump/section means same may serve both functions, or that, for example, a pump only for dosing system is mounted at the inlet, and suction means only for withdrawing communicate with the outlet.

Figure 7:
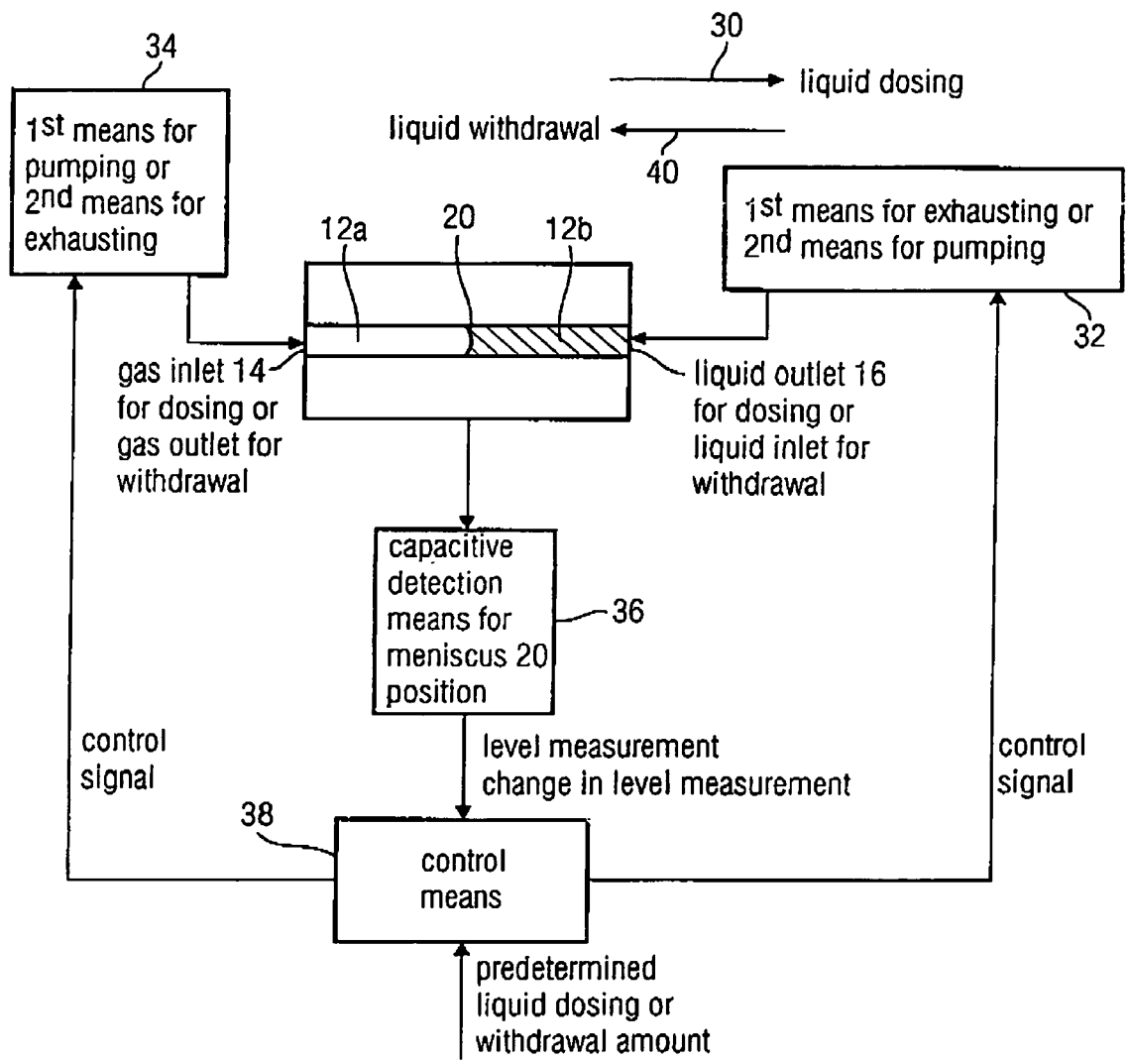
FIG. 7 shows a block diagram of the inventive dosing system, the inventive withdrawal system or the inventive combined dosing/withdrawing system.

FIG. 7 shows the inventive dosing system, the inventive withdrawing system or the inventive combined dosing/withdrawing system. First of all, the inventive dosing system is described. In this case, the liquid dosing from the liquid outlet 16 is performed as indicated by an arrow 30 in FIG. 7. To this end, block 32 illustrates only a means for exhausting, and block 34 only illustrates a means for pumping. It is clear that in order to perform a liquid dosing, either a means for exhausting in block 32 or a means for pumping in block 34 are sufficient. Naturally, one can also use the means for pumping in block 34 as well as the means for exhausting in block 32. The capacitive detection means performs a detection of the position of the meniscus 20 in order to output a level measurement or a change in level measurement to the control means 38. The control means 38 forwards a control signal either to the means for pumping in block 34 or to the means for exhausting in block 32 or to the means for pumping in block 34 as well as the means for exhausting in block 32. The control means is operative to provide the control signal dependent on the level measurement or the change in level measurement and the predetermined liquid dosing amount.

Alternatively, the inventive device in FIG. 7 can also serve as a liquid withdrawal apparatus as indicated by arrow 40. In this case, the situation is contrary to the situation, when the device functions as a liquid dosing system. This means that block 32 only includes the means for pumping the predetermined withdrawal amount from the outside into the channel.

Alternatively, block 34 includes only the means for exhausting gas from the channel which also results in a movement of the meniscus 20 from left to right, so that the channel includes more liquid after the withdrawal action compared to the case before the withdrawal action. As in the dosing device, liquid withdrawal can also be performed by the means for exhausting gas from section 12a of the channel as well as the means for pumping liquid into outlet 16 as indicated in block 32.

In the third embodiment of the present invention, the invention device is a combined dosing/withdrawal device. In this case, block 32 includes the first means for exhausting liquid from the outlet to perform dosing. Alternatively, the device only includes the first means for pumping gas into the section 12a of the channel to perform an outlet of liquid at the liquid outlet 16. Additionally, block 32 can also include the second means for exhausting gas from section 12a of the channel to perform withdrawal of liquid into the channel. The withdrawal operation can also be performed by the second means for pumping in block 32 either in addition to the second means for exhausting or instead of the means for exhausting.

To summarize, all embodiments have in common that the capacitive detection means detects the position of the meniscus in order to output a level measurement or a change in level measurement which is input into the control means 38 which, depending on the level measurement and the change in level measurement as well as the predetermined liquid dosing amount or the predetermined liquid withdrawal amount forwards respective control signals to block 34 or 32.

What is claimed is:

1. Dosing system for dosing a predetermined amount of liquid, comprising:
    a liquid reservoir with level measurement, comprising:
    a base body;
    a channel implemented in the base body and having an inlet and an outlet, the dimensions of a cross-section of the channel being selected such that a liquid when filled into the channel forms a liquid meniscus which demarcates a section of the channel filled with liquid from an unfilled section of the channel in which no liquid is present,
    wherein the dimensions of the cross-section of the channel, the liquid and a material of the channel are selected such that the position of the liquid meniscus in relation to the channel being substantially independent of the orientation of the liquid reservoir; and
    detection means for detecting the position of the liquid meniscus in relation to the channel so as to obtain a level measurement or a change in level measurement of the liquid reservoir by detecting the position of the liquid meniscus;
    means for exhausting the predetermined amount of liquid, the means for exhausting being connected to the outlet of the channel, or means for pumping gas into the unfilled section of the channel, the means for pumping being connected to the inlet of the channel; and
    control means for controlling the means for exhausting and the means for pumping, the control means coupled to the detection means of the liquid reservoir so as to obtain the level measurement or the change in level measurement and to control the means for exhausting and the means for pumping to dispense the predetermined amount of liquid from the channel via the outlet of the channel, depending on the level measurement or the change in level measurement;

wherein the detection means are capacitive and comprise two electrodes electrically insulated from each other and mounted on the base body such that both the filled and the unfilled section of the channel extend between same, wherein an electric field to be generated between the two electrodes is present both in the filled section of the channel and in the unfilled section of the channel, and wherein a change in the position of the liquid meniscus leads to a proportional change in capacitance.

2. Withdrawal system for withdrawing a predetermined amount of liquid, comprising:

a liquid reservoir with level measurement, comprising:
a base body;
a channel implemented in the base body and having an inlet and an outlet, the dimensions of the channel cross-section being selected such that a liquid when filled into the channel forms a liquid meniscus which demarcates a section of the channel filled with liquid from an unfilled section of the channel in which no liquid is present;
wherein the dimensions of the cross-section of the channel, the liquid and a material of the channel are selected such that the position of the liquid meniscus in relation to the channel being substantially independent of the orientation of the liquid reservoir; and
detection means for detecting the position of the liquid meniscus in relation to the channel so as to obtain a level measurement or a change in level measurement by detecting the position of the liquid meniscus;
means for pumping a liquid into the liquid reservoir the means for pumping being connected to the outlet of the channel, or means for exhausting gas from the unfilled section of the channel exhausting being connected to the inlet of the channel; and
control means for controlling the means for pumping and the means for exhausting, the control means being coupled to the detection means of the liquid reservoir so as to obtain the level measurement or the change in level measurement and to control the means for exhausting and the means for pumping to convey a predetermined amount of liquid into the channel via the outlet of the channel depending on the level measurement or the change in level measurement;
wherein the detection means are capacitive and comprise two electrodes electrically insulated from each other and mounted on the base body such that both the filled and the unfilled section of the channel extend between same, wherein an electric field to be generated between the two electrodes is present both in the filled section of the channel and in the unfilled section of the channel, and wherein a change in the position of the liquid meniscus leads to a proportional change in capacitance.

3. Dosing system as claimed in claim 1, wherein the channel is folded in a meander-like fashion so as to obtain a comparatively long channel in relation to outer dimensions of the base body.

4. Dosing system as claimed in claim 1, wherein the base body is a hose, and the channel is formed by the opening of the hose.

5. Dosing system as claimed in claim 1, wherein the channel has elliptical and preferably circular cross-sectional dimensions, the small axis of the elliptical cross-section and/or the diameter of the circular cross-section being selected to be so small that the position of the meniscus is determined substantially by the surface tension of the liquid as well as by the interfacial tension between the liquid and the material of the channel wall, whereas gravity has substantially no influence on the position of the meniscus.

6. Dosing system as claimed in claim 1, wherein the channel has rectangular cross-sectional dimensions, the small side of the rectangular cross-sectional dimensions being selected so small that the position of the meniscus is determined substantially by the surface tension of the liquid as well as by the interfacial tension between the liquid and the material of the channel wall, whereas gravity has substantially no influence on the position of the meniscus.

7. Dosing system as claimed in claim 1, wherein the length of the channel is selected such that, with the liquid reservoir filled as directed, the section of the channel in which no liquid is present has a minimum length determined by an admissible evaporation rate for the liquid.

8. Dosing system as claimed in claim 1, wherein in the section of the channel in which no liquid is present, with the liquid reservoir filled as directed, a constriction is present, the cross-sectional dimensioning of which is influenced by admissible evaporation rate.

9. Dosing system as claimed in claim 1, wherein a sealing in the form of a semi-permeable membrane which is impermeable for liquid molecules is present at the inlet.

10. Dosing system as claimed in claim 1, wherein the base body is a hose, and wherein both electrodes are arranged on the outer surface of the hose and extend along the length of the hose.

11. Dosing system as claimed in claim 1, wherein the base body is a hose, and wherein one electrode is arranged on the outer surface of the hose, and the other electrode is positioned within the hose and is separated from the liquid by an insulating layer by means of conductive separation.

12. Dosing system as claimed in claim 1,
wherein one electrode is implemented as a bottom electrode, and wherein the other electrode is implemented as a cap electrode, the channel present in the base body being directly bounded by the bottom and cap electrodes or being bounded by an electrically insulating layer between the bottom electrode and the channel and by an electrically insulating layer between the cap electrode and the channel, the electrically insulating layers being implemented integrally with the base body and/or the bottom and cap electrodes.

13. Dosing system as claimed in claim 12, wherein the cap electrode, the bottom electrode or both are implemented as grid electrodes so as to be able to optically detect any gas bubbles in the filled section of the channel.

14. Dosing system as claimed in claim 12, wherein the cap electrode and/or the bottom electrode consist of a plurality of individual electrodes, so that a plurality of individual capacitances are formed between the bottom electrode and the cap electrode, the individual capacitances being determinable independently of each other so as to capacitively detect any gas bubbles in the filled section.

15. Dosing system as claimed in claim 1, wherein both electrodes are arranged vertically in relation to main surfaces of the base body and each extend along the channel.

16. Dosing system as claimed in claim 1, wherein the detection means are arranged so as to optically monitor the level in the channel, and wherein the channel is optically transparent on at least one side of same so that an evaluation of the filling quality is to be performed manually or automatically.

17. Combined dosing/withdrawal system for dosing a predetermined amount of liquid or for withdrawing a predetermined amount of liquid, comprising:

a liquid reservoir with level measurement, comprising:

a base body;

a channel implemented in the base body and having an inlet and an outlet, the dimensions of the channel cross-section being selected such that a liquid when filled into the channel forms a liquid meniscus which demarcates a section of the channel filled with liquid from an unfilled section of the channel in which no liquid-s present;

wherein the dimensions of the cross-section of the channel, the liquid and a material of the channel are selected such that the position of the liquid meniscus in relation to the channel being substantially independent of the orientation of the liquid reservoir; and detection means for detecting the position of the liquid meniscus in relation to the channel so as to obtain a level measurement or a change in level measurement by detecting the position of the liquid meniscus;

first means for pumping a liquid into the liquid reservoir or for exhausting a liquid from the liquid reservoir, the first means for pumping or exhausting being connected to the outlet;

second means for exhausting gas from the unfilled section of the channel or for pumping gas into the unfilled section of the channel the second means for exhausting or pumping being connected to the inlet; and control means for controlling the first means and the second means, the control means being coupled to the detection means of the liquid reservoir so as to obtain the level measurement or the change in level measurement and to control the means for exhausting and the means for pumping to convey the predetermined amount of liquid into the channel via the outlet of the channel or to dispense the predetermined amount of liquid from the channel via the outlet of the channel, depending on the level measurement or the chance in level measurement;

wherein the detection means are capacitive and comprise two electrodes electrically insulated from each other and mounted on the base body such that both the filled and the unfilled section of the channel extend between same, wherein an electric field that may be generated between the two electrodes is present both in the filled section of the channel and in the unfilled section of the channel, and wherein a change in the position of the liquid meniscus leads to a proportional change in capacitance.

\* \* \* \* \*